United States Patent [19]

Freston

[11] Patent Number: 5,244,679
[45] Date of Patent: Sep. 14, 1993

[54] TOPICAL PREPARATIONS FOR ALLEVIATION OF MINOR HUMAN SKIN IRRITATIONS

[76] Inventor: Ann Freston, Star Rte., Box 5A, Roosevelt, Utah 84066

[21] Appl. No.: 852,032

[22] Filed: Mar. 16, 1992

[51] Int. Cl.$^5$ .................. A61K 33/22; A61K 33/02; A61K 31/20; A61K 31/045

[52] U.S. Cl. ...................... 424/659; 424/719; 514/558; 514/738; 514/786

[58] Field of Search ............ 514/786, 738, 558; 424/719, 659

[56] References Cited

U.S. PATENT DOCUMENTS

| | | | |
|---|---|---|---|
| 2,172,118 | 9/1939 | Blish | 514/558 |
| 3,696,193 | 10/1972 | Guglielmetti et al. | 514/360 |
| 4,165,385 | 8/1979 | Lefebvre | 514/783 |
| 4,370,319 | 1/1983 | Chapin et al. | 514/772 |
| 4,375,465 | 3/1983 | Drakoff | 514/553 |
| 4,478,853 | 10/1984 | Chausser | 514/772 |

OTHER PUBLICATIONS

Remington's Pharmaceutical Science, 15th edition, Mack Publishing Company, pp. 1250, 1254–1255, 1257, 1258, 1268.

Primary Examiner—Marianne M. Cintins
Assistant Examiner—Rebecca Cook
Attorney, Agent, or Firm—K. S. Cornaby

[57] ABSTRACT

A topical preparation for aiding in the care of minor skin irritations, such as chapping, reddening, tenderness, and the like, has as its constituents a mixture of glycerin, stearic acid, cocoa butter and boric acid blended together in a creamy base.

2 Claims, No Drawings

TOPICAL PREPARATIONS FOR ALLEVIATION OF MINOR HUMAN SKIN IRRITATIONS

BACKGROUND OF THE INVENTION

The present invention relates to topical preparations for alleviation of minor human skin irritations.

For many years, research has been conducted into causes of, and remedies for, minor skin rashes on humans. Such rashes can be caused by allergies, exposure of the skin to periods of cold weather, or exposure to hot, humid conditions, such as washing dishes or the like. These rashes can also be caused by excessive dryness of the skin without adequate moisturizing of the skin.

While the causes may vary, the symptoms usually involve minor skin irritating skin eruptions, chaffing and chapping accompanied by pain and discomfort. Over the years, numerous attempts have been made to develop topical creams and ointments that relieve or sooth the pain and/or itchiness which so often accompany such skin irritations. Suggested prior art solutions include those found in U.S. Pat. Nos. 4,427,670; 4,375,465; 4,478,853; and 4,370,319.

It is therefore an objective of this invention to provide a topical skin preparation which will alleviate the symptoms of minor skin eruptions, redness, dryness, rashes, and chapping in human beings.

SUMMARY OF THE INVENTION

A topical preparation for the alleviation of the symptoms of human skin irritations, including chapping, reddening, and tenderness is provided which includes glycerin, stearic acid, cocoa butter and boric acid blended together in a cream-like base.

DETAILED DESCRIPTION OF PREFERRED EMBODIMENTS

A number of formulations of the invention have been made which can be employed to aid in the care of minor human skin irritations. Several examples of preferred embodiments of the invention follow to illustrate the range of formulations available within the scope of the invention.

EXAMPLE NO. 1

Lotion

Ingredients:
1¼ C glycerin
5 oz. stearic acid
1 bar cocoa butter [1 oz.]
1 T ammonia
½ tsp boric acid
2 C warm water Formulation Process:
Place glycerin, stearic acid, and cocoa butter in a container over hot water. Stir until dissolved, add ammonia. Continue over heat until mixture is smooth. Remove from heat and blend until mixture turns white. Dissolve boric acid in warm water, add to white mixture, and mix 10 minutes.

EXAMPLE NO. 2

Hand Cream

Ingredients:
1 C glycerin
3 oz. stearic acid
½ bar cocoa butter
1 T ammonia
½ tsp boric acid
1½ C water Formulation Process:
Place glycerin, stearic acid, and cocoa butter in a container over hot water. Stir until dissolved, add ammonia. Continue over heat until mixture is smooth. Remove from heat and blend until mixture turns white. Dissolve boric acid in warm water, add to white mixture, and mix 10 minutes.

EXAMPLE NO. 3

Hand Cream

Ingredients:
1¼ C glycerin
4 oz. stearic acid
½ bar cocoa butter
¾ T ammonia
¼ tsp boric acid
1¾ C water Formulation Process:
Place glycerin, stearic acid, and cocoa butter in a container over hot water. Stir until dissolved, add ammonia. Continue over heat until mixture is smooth. Remove from heat and blend until mixture turns white. Dissolve boric acid in warm water, add to white mixture, and mix 10 minutes.

EXAMPLE NO. 4

Hand Cream

Ingredients:
2 C glycerin
7 oz. stearic acid
1½ bars cocoa butter
1½ T ammonia
1 tsp boric acid
2½ C water Formulation Process:
Place glycerin, stearic acid, and cocoa butter in a container over hot water. Stir until dissolved, add ammonia. Continue over heat until mixture is smooth. Remove from heat and blend until mixture turns white. Dissolve boric acid in warm water, add to white mixture, and mix 10 minutes.

EXAMPLE No. 5

Hand Cream

Ingredients:
1¾ C glycerin
6 oz. stearic acid
1 bar cocoa butter
1¼ T ammonia
¾ tsp boric acid
2¼ C water Formulation Process:
Place glycerin, stearic acid, and cocoa butter in a container over hot water. Stir until dissolved, add ammonia. Continue over heat until mixture is smooth. Remove from heat and blend until mixture turns white. Dissolve boric acid in warm water, add to white mixture, and mix 10 minutes.

While this invention has been described in a preferred embodiment, it will be understood that there are substantial equivalents which fall within the scope of the appended claims.

I claim:

1. A topical composition for alleviating the symptoms of human skin irritations comprising from 1 C to 2 C glycerin; from 3 oz. to 6 oz. stearic acid; from ½ to 1 bar of cocoa butter; from ½ to 1¼ T ammonia, and from ½ to 1 tsp. boric acid.

2. A process for making a composition for alleviating the symptoms of human skin irritations comprising the steps of:

placing glycerin, stearic acid and cocoa butter in a container over hot water to form a mixture;

stirring said mixture over hot water until dissolved;

adding ammonia and continuing to heat until mixture is smooth;

removing mixture from heat and blending until mixture turns white;

dissolving boric acid in warm water;

adding dissolved boric acid to said mixture; and mixing combination of boric acid and mixture for 10 minutes wherein the ingredients are introduced into the mixture in the following amounts: from 1 C to 2 C glycerin; from 3 oz. to 6 oz. stearic acid; from ½ bar to 1 bar of cocoa butter; from ½ to 1¼ T ammonia, and from ½ to 1 tsp. boric acid.

* * * * *